United States Patent [19]
Nolting et al.

[11] Patent Number: 5,211,053
[45] Date of Patent: May 18, 1993

[54] HOT GAS SENSOR DEVICE WITH IMPROVED THERMAL ISOLATION FROM CARRIER PLATE

[75] Inventors: Peter Nolting, Buehlertal; Martin Holland, Merzhausen; Botho Ziegenbein, Reutlingen; Guenther Stecher, Leonberg; Detlef Baresel, Stuttgart, all of Fed. Rep. of Germany

[73] Assignee: Robert Bosch GmbH, Stuttgart, Fed. Rep. of Germany

[21] Appl. No.: 838,545

[22] Filed: Feb. 19, 1992

[30] Foreign Application Priority Data

Feb. 19, 1991 [DE] Fed. Rep. of Germany ....... 4105025

[51] Int. Cl.$^5$ ............................................. G01N 27/12
[52] U.S. Cl. .................................. 73/31.05; 73/31.06; 422/98; 338/34
[58] Field of Search ................... 73/31.05, 31.06, 23.2, 73/25.05; 338/34; 422/88, 90, 98; 304/424, 431

[56] References Cited

U.S. PATENT DOCUMENTS

| | | | |
|---|---|---|---|
| 4,241,019 | 12/1980 | Nakatani et al. | 73/23.31 |
| 4,338,281 | 7/1982 | Treitinger et al. | 422/98 |
| 4,706,493 | 11/1987 | Chang et al. | 73/31.06 |
| 4,847,783 | 7/1989 | Grace et al. | 422/98 X |
| 4,991,424 | 2/1991 | Lehto | 73/31.06 |
| 5,019,885 | 5/1991 | Yagawara et al. | 338/34 X |

FOREIGN PATENT DOCUMENTS

| | | |
|---|---|---|
| 0291462A2 | 11/1988 | European Pat. Off. |
| 0323937A1 | 7/1989 | European Pat. Off. |
| 3019387A1 | 11/1981 | Fed. Rep. of Germany |
| 0275648 | 12/1986 | Japan ............................. 73/31.05 |

*Primary Examiner*—Hezron E. Williams
*Assistant Examiner*—Michael J. Brock
*Attorney, Agent, or Firm*—Frishauf, Holtz, Goodman & Woodward

[57] ABSTRACT

A gas sensor device has a carrier plate of ceramic or glass. The carrier has apertures which leave only strips in a spiral configuration connecting a middle region of the carrier to the outer region thereof. The apertures may be mere slits separating the connection strips or they may be apertures providing larger air gaps. On each middle region so provided on the carrier a sensor element is located that has two electrodes and a sensitive layer which establishes a conducting connection between the electrodes. The electrodes and the sensitive layer are directly applied to the upper surface of the middle region. The two electrodes are comb shaped and are placed in inter-digital configuration to define a meandering gap between them. On the underside of the middle region of the carrier a heating element for the sensor element is provided and, if desired, also a temperature measuring resistance for regulating the temperature produced by a heating resistor. Conducting paths are located on the connecting strips between the middle region and the outer region of the carrier for connecting a sensor element and its heater to circuits on the outer region of the carrier plate.

17 Claims, 2 Drawing Sheets

HOT GAS SENSOR DEVICE WITH IMPROVED THERMAL ISOLATION FROM CARRIER PLATE

This invention concerns an electrical hot gas sensor device of the kind in which a carrier plate of ceramic or other electrically insulating and heat resistant material has an outer region and at least one middle region surrounded by the outer region but separated from it by gaps bridged by a few connecting strips. A sensor element is mounted on such an inner region and has two electrodes applied to the carrier plate there, separated from each other by a gap, while a sensitive layer provides a conductive connection between the electrodes. The sensitive layer changes its conductivity in accordance with the content of the hot gas to which it is exposed. An electrical heating element is provided near the electrodes and conducting paths are provided connecting the sensor element and the heating element to circuits located at least in part on the outer region of the carrier plate, passing from the middle region to the outer region on the aforesaid conducting strips which bridge the gaps that largely isolate the middle region from the outer region of a carrier plate.

BACKGROUND AND PRIOR ART

In European Patent application 0 323 937 a gas sensor is described which has a carrier on which the sensor element is applied by means of thin film or even thick film technology. A small plate of electrically insulating material, such as glass, silicon oxide or ceramic, for instance, serves as the carrier for the sensor element. This carrier has rectangular apertures that are so configured that a middle region and an outer region are formed which are connected by strips between elongate apertures. A resistance layer for heating the sensor element is first applied to the middle region of the carrier. Above this resistance layer is an electrically insulating layer deposited thereon. On top of that are two electrodes facing each other across a gap and having a connection to each other through a sensitive layer which also covers them. The electrical contacting of the resistance layer and of the two electrodes of this layering construction is provided over conducting paths deposited on the carrier and passing across the strips connecting the middle and outer regions thereof.

In the gas sensor device described in the above-identified document, arrays of connecting strips are in a straight line configuration. In order to obtain good thermal insulation of the middle region from the outer region of the carrier, the connecting strips must be made very thin, since they are also relatively short. The electrodes of the sensor element above referred to are either rectangular or have dot shaped surfaces. Such sensor elements are of relatively high ohmic resistance, which is a disadvantage with respect to the measurement range of the gas sensor.

It is an object of the present invention to provide a gas sensor of the above described general kind in which the middle portions of the carrier plate which carry a sensor element are better isolated thermally from the outer region of the carrier plate, so that related components and circuits can be mounted in that outer region to better advantage and construction of the device can be simple and efficient.

Briefly, the connecting strips of the carrier plate extending outward from a middle region to the outer region are of a spiral configuration around the middle region supported by them. The sensor element components, two electrodes and a sensitive layer, are applied directly to the upper surface of the middle region of the carrier. The two electrodes are comb shaped and oppose each other in an interdigital configuration defining a meandering gap. The heating element is on the lower surface of the middle region in each case.

The sensor device of the invention has a particularly simple construction. By mounting the heating element on the underside of the mid-region of the carrier and the provision of the electrodes and the sensitive layer of the sensor element directly on the upper surface of the mid-region of the carrier simplifies the manufacture of the sensor device compared with manufacture of the heretofore conventional structure.

The use of the carrier substrate itself as an electrically insulating layer between the heating element and the sensor element is particularly advantageous when a thin ceramic substrate is used, because in that case heat exchange between the front and the back side of the carrier plate takes place very quickly. The provision of the sensor element directly on the upper side of the carrier substrate is also advantageous, because it is then possible to provide not only thick film sensor elements, as for example $SnO_2$ sensor elements, or, alternatively, thin film sensor elements, such as phthalocyanine sensor elements. The spiral configuration of the connecting strips around the middle region of the carrier plate supported by them produces a particularly good thermal decoupling of the middle region, with its heating element and sensor element, from the outer region of the carrier plate. Since the connecting strips are comparatively long, these can be designed to be substantially more stable and firm than has been the practice heretofore. The spiral structure of the connecting strips also has the advantage of providing a comparatively small space requirement for the sensor device.

The interdigital configuration of the electrodes is advantageous because in this way there is the equivalent of a parallel connection of many resistance elements, so that the aggregate resistance of the sensor layer lying above them is greatly reduced. The aggregate resistance of the sensor element thereby varies under adsorption of noxious gases over a readily accessible resistance range for measurement.

A useful further development of the invention is to locate a temperature-measuring resistance on the underside of a middle region of the carrier plate, in addition to the heating element already mentioned, for providing the necessary exact temperature control for the heating element. It is also useful from the manufacturing point of view to provide the heating element in the form of heating resistors, so that the heating resistances and the temperature measuring resistances can first be printed as closed thick film surfaces and then structurized (cut out) by laser cutting.

With a suitable choice of resistance disposition and heat regulation, a homogenous distribution of temperature affecting the sensing element is obtained.

It is particularly convenient to provide feed-through contacts passing through the mid-region of the carrier plate for connection of the heater and the heat regulating resistance to circuits on the upper side of the carrier. The feed-throughs can be provided, for example, in thick film technology. In that way a substantial simplification of the manufacturing technology is obtained. In the mode of construction according to the invention, the heating power and likewise the loss power of the heat regulation circuit can be kept relatively small. For this purpose it is possible for the heat regulation, with its power dissipating components, and likewise at least part of the evaluation circuit, to be provided on the carrier plate in its outer region, thus providing an advantageous saving of space. The overall construction of at least part of the sensor device of the invention is thus economically and easily handled in thick film and/or thin film technology.

The good thermal decoupling of the gas sensor according to the invention makes possible the integration of many different sensor elements with an evaluation circuit on a carrier substrate. Good thermal decoupling of the individual sensor elements with respect to each other and with respect to the carrier substrate is important for thermodynamic reasons, because the sensor elements change their resistance value by adsorption of noxious gases, as for example CO and $NO_x$. They are driven at high temperature (about 150° C. to 500° C.) for amplification of the effect just mentioned.

It is advantageous to dispose the completed sensor module, including the sensor elements, the heat regulation and the evaluation circuit, in a casing at least in part sub-divided into chambers, so that the evaluation circuit is undisturbed in a closed-off part of the casing, while every sensor element is located in a ventilated part of the casing. It is particularly advantageous in such a case to guide the gas mixture to be investigated so that it passes through a filter for filtering out special components of the gas mixture to be investigated by the respective sensor elements. A ventilator driven by a motor is advantageously be integrated in the casing, since that makes it possible to guide a gas or particle stream at constant speed over the sensor elements. The possibility of integrating filters into the sensor device construction and, optionally, a ventilator with a ventilation motor, leads to a particularly compact structure of a gas sensor device.

DESCRIPTION OF THE DRAWINGS

The invention is further described by way of illustrative example with reference to the annexed drawings, in which:

FIG. 1b showing a configuration different from that shown in FIG. 1a;

DESCRIPTION OF THE ILLUSTRATED EMBODIMENTS

Figure 1A:
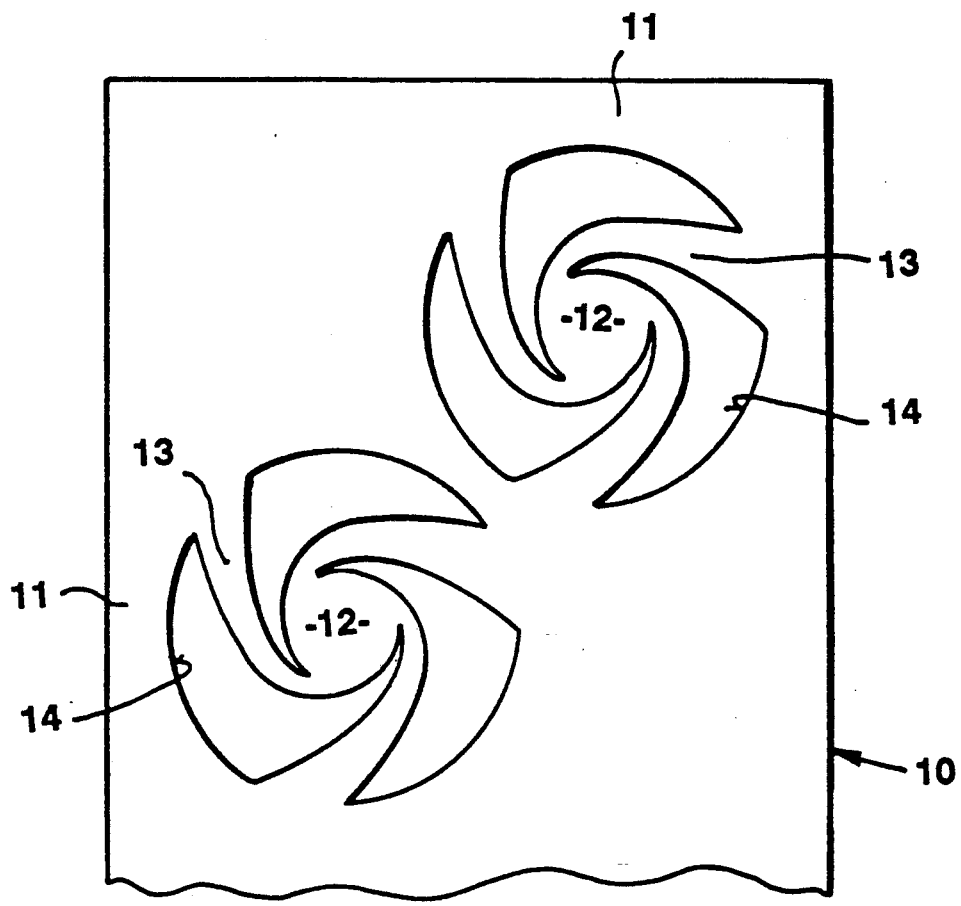
FIGS. 1a and 1b show a partial plan view of a carrier plate having one or more isolated middle regions in accordance with the invention.

FIG. 1a shows a carrier 10 of an electrically insulating material, for example of ceramic or glass. The carrier 10 has apertures 14 that are so arranged that three apertures 14 always surround a mid-region 12, which is then connected with an outer region 11 only over the strips 13. The apertures 14 are so dimensioned and disposed that the strips 13 have a spiral configuration around the mid-region 12. In that way long holding arms can be provided in a highly space-saving way, while at the same time providing high stability of the structure and, in addition efficient thermal isolation of the middle region 12 from the outer region 11 of the carrier 10.

Figure 1B:
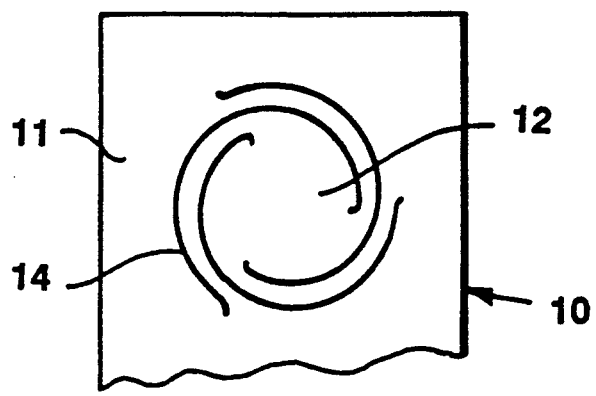

The apertures 14 could, for example, be produced by laser cutting into the carrier 10. This can be done even with simple slits as shown in FIG. 1b, or it can be done for cutting out segments of the area material as shown in FIG. 1a. There is the further possibility of stamping out the apertures beforehand from the unsintered (green) ceramic, before the plate is fired into its hard form.

Figure 2:
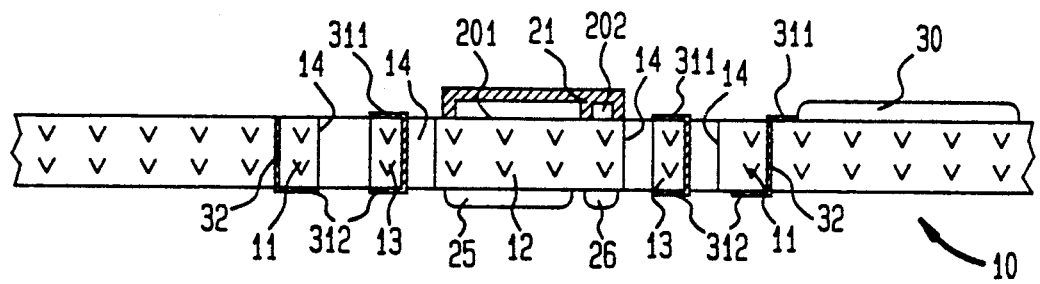
FIG. 2 is a cross section through a carrier plate equipped with circuit elements.

FIG. 2 shows a section through a carrier plate 10 which has been structurized as in FIG. 1a and which has been provided with circuit elements corresponding to the function of the gas sensor. On the upper side of the middle region 12 of the carrier 10 are two electrodes 201 and 202 disposed so that they can face each other edgewise (see FIG. 3). Extending over the electrodes there has been deposited a sensitive layer 21 which provides an electrically conducting connection between the two electrodes 201 and 202. On the underside of the middle region 12 a heating resistor 25 and a temperature-measurement resistance 26 are applied. The middle region 12 is separated from the outer region 11 by the apertures 14 and is connected with the outer region 11 only through the spiral configuration of strips 13. Conducting paths 311, 312 are deposited on the underside of the strips 13 and extend over to the outer region 11.

Over these conducting paths 311 and 312 the two electrodes 201 and 202 as well as the heating resistor 25 and the temperature measurement resistance 26 are electrically accessible. In the embodiment of a gas sensor device according to the invention shown in FIG. 2, through contacts 32 penetrating through the carrier 10 are located in the outer region 11, by virtue of which the circuit elements on the underside of the middle region 12, in this case the resistances 25 and 26, are also electrically accessible from the upper side of the carrier 10. Both the evaluation circuit 30 and also a heat regulator 35 not shown in FIG. 2 are located on the upper side of the carrier 10 in its outer region 11. The provision of the individual circuit elements on the carrier 10 in accordance with FIG. 2 can be carried out in thick film or thin film technology. Thus it is possible, for example, to structurize the heating resistance 25 and the temperature measuring resistance 26 first as a closed thick film resistance surface on the underside of the middle region 12 of the carrier 10 by printing onto the carrier and then to structurize the thick film by laser cutting. For the two electrodes 201 and 202 and the sensitive layer 21 of the sensor element, there come into consideration not only implementation in thick film technology, but also manufacture in thin film technology, since these components are applied directly onto the carrier 10. The conducting paths 311 and 312 can also be produced either in thick film or, if desired, in thin film technology. The provision of feed-through contacts for electrical connection of resistances 25 and 26 on the underside of the middle region 12 of the carrier 10 is performable in a standard process of thick film technology.

The measurement principle of the sensor shown in FIG. 2 is based on the fact that the aggregate resistance of the combination of the two electrodes 201 and 202 with the sensitive layer 21 changes according to the quantity of noxious gas absorbed or adsorbed by the sensitive layer 21. The gas mixture to be investigated is therefore guided over the upper side of the carrier 10 to which the sensor element is affixed. The change in resistance of the sensor element is detected and is evaluated in the evaluation circuit 30. For thermo-dynamic reasons the sensor elements are operated at temperatures of about 150° C. to about 500° C. according to the kind of noxious gas that is to be detected. The heating of the sensor element is produced by the heater resistance 25 on the underside of the middle region 12 of the carrier 10, but could also be produced by another heating device. The temperature measuring resistance 26 serves for providing exact temperature regulation, since the quality of the measurement result depends decisively from the presence of a homogeneous temperature distribution at the sensor element. By means of the structure of the strips 13 according to the invention, the thermal decoupling of the middle region 12 from the outer region 11 of the carrier 10 is so good that a number of separately heatable sensor elements can be mounted respectively on corresponding middle regions 12 of a carrier. They can each be installed for detection of a different noxious gas. This good thermal decoupling also makes it possible for the evaluation circuit as well as the heat regulation with power dissipating components to be disposed on the remaining portion of the carrier, namely on the outer region 11 thereof.

Figure 3:
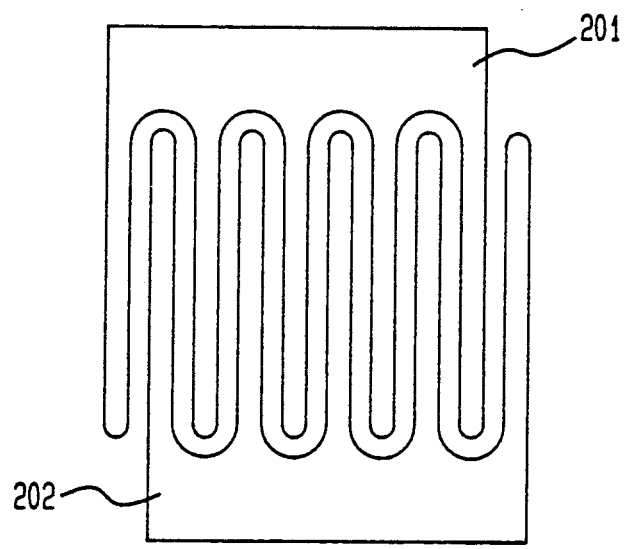
FIG. 3 is a top view of an electrode configuration of a sensor element.

FIG. 3 shows an advantageous embodiment of the electrodes 201 and 202. In accordance with the invention they are made in comb shape so that they can be fitted together in an interdigital arrangement, above which the sensitive layer 21 can be deposited. This special embodiment operates as a parallel connection of a large number of high-ohm resistances and serve for reducing the aggregate resistance of the sensor element so that the aggregate resistance is in a good range for measurement. In consequence, the measurement of resistance changes can be determined exactly.

Figure 4:
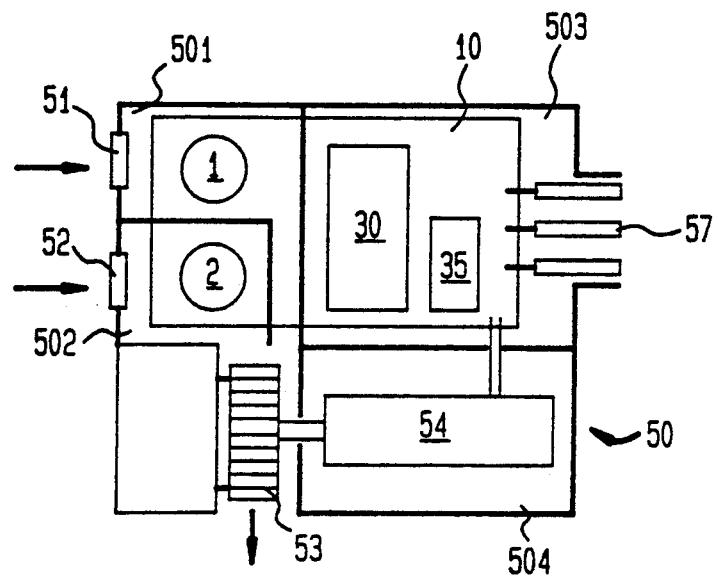
FIG. 4 is a schematic top view of a gas sensor device having a casing.

In FIG. 4 a casing 50 is shown which has a number of chambers 501, 502, 503 and 504 partitioned within it. The carrier 10 with the sensor elements 1 and 2 as well as the evaluation circuit 30 and the heat regulation unit 35 are so built into the casing 50 that the evaluation circuit 30 and the heat regulation circuit 35 are disposed in the closed-off chamber 503. The plug connector 57 for the sensor serves for connection to the interior of the chamber 503. The sensor elements 1 and 2 are respective located in chambers 501 and 502. These chambers can be ventilated by means of a ventilator 53 which is connected to a ventilation motor 54 disposed in a fourth chamber 504. Also located in the outer walls of the chambers 501 and 502 are, respectively, the filters 51 and 52 that, if desired, can be used for pre-measurement preparation of the gas mixture to be investigated. By means of the ventilator 53 and ventilation motor 54 integrated into the housing 50 a gas or particle stream of constant velocity can be led over the sensor elements 1 and 2. Thus the gas sensor device equipped with a casing as shown in FIG. 4 in accordance with the invention is distinguished by a highly compact construction volume.

Although the invention has been described with reference to particular illustrative embodiments, it would be understood that variations and modifications are possible are within the inventive concept.

We claim:

1. An electrical hot gas sensor device, comprising:
a carrier plate of an electrically insulating material selected from the group consisting of ceramics and other heat-withstanding solid materials, said carrier plate having an upper surface and a lower surface and having an outer region and at least one middle region surrounded by said outer region but separated from said outer region by gaps bridged by a plurality of connecting strips;
at least one sensor element mounted on said at least one inner region, having two electrodes on said carrier plate separated from each other by a gap and having a sensitive layer providing a conductive connection between said electrodes;
at least one electrical heating element for said at least one sensor element and electrically conducting paths on said connecting strips, some electrically connected to said at least one sensor element and others electrically connected to said at least one heating element and all connected to circuits located in part on said outer region of said carrier plate, characterized in that:
said connecting strips (13) extend outward from said at least one middle region (12) in a spiral configuration extending around said at least one middle region (12);
said at least one sensor element (1) with its two electrodes (201, 202) and sensitive layer (21) is applied to said upper carrier surface within said at least one middle region (12);
said two electrodes of a said at least one sensor element lie flat on said middle region of said carrier plate and have, together, an interdigital configuration defining a meandering gap between them, each of said two electrodes of a said sensor having the configuration of a comb with teeth extending in between the teeth of the other; and
said at least one heating element (25) is affixed to said lower surface of said at least one middle region (12) of said carrier plate.

2. The electrical hot gas sensor device of claim 1, wherein said at least one electrical heating element (25) is constituted by at least one heating resistance.

3. The electrical hot gas sensor device of claim 1, wherein at least one temperature-measuring resistance (26) is provided on said lower surface of said carrier in said at least one middle region (12) for control of the temperature of said at least one heating element and is connected in circuit for that purpose.

4. The electrical hot gas sensor device of claim 3, wherein through contacts (32) are provided passing through said carrier plate from said upper surface to said lower surface of said carrier plate (10) and are connected respectively to said at least one heating element and to said at least one temperature measuring resistance (26) for connecting said at least one heating element and said at least one temperature measuring resistance with respective circuits that lie at least in part on said upper surface of said carrier plate.

5. The electrical hot gas sensor device of claim 4, wherein at least one of an evaluation circuit (30) and a heat regulating circuit (35) is located on said outer region (11) of said carrier plate (10).

6. The electrical hot gas sensor device of claim 5, wherein:
said at least one sensor element (1, 2);
said at least one heating element (25);
said at least one temperature measuring resistance (26);
said electrically conducting paths on said connecting strips;
said through contacts (32), and
said at least one heat regulating circuit (35) are provided on said carrier at least in part in thick film technology or in thin film technology, or in part in thick film technology and in part in thin film technology.

7. The electrical hot gas sensor device of claim 6, wherein:
said at least one sensor element (1, 2) is situated in a gas flow duct and accessible to gas therein and wherein a casing (50) is provided for said hot gas sensor device having a multiplicity of outer chambers (501, 502, 503, 504), whereby said evaluation circuit (30) and said at least one heat regulation circuit (35) are located in at least one of said chambers (503) which are closed off against said gas flow, whereas said at least one sensor element (1, 2) is located in another chamber (501, 502) through which gas to be investigated by said at least one sensor flows.

8. The electrical hot gas sensor device of claim 7, comprising also a ventilator (53) equipped with a controllable ventilator motor (54) for controlling the gas supply to said at least one sensor element (1, 2).

9. The electrical hot gas sensor device of claim 7, wherein at least one filter (51, 52) is provided for filtering the gas flowing through said at least one chamber.

10. The electrical hot gas sensor device of claim 4, wherein a plurality of heat regulating circuits is located on said outer region (11) of said carrier plate (10).

11. The electrical hot gas sensor device of claim 3, wherein at least one through contact (32) is provided passing through said carrier plate from said upper surface to said lower surface of said carrier plate (10) and is connected to said at least one heating element for connecting the same with a circuit that lies at least in part on said upper surface of said carrier plate.

12. The electrical hot gas sensor device of claim 11, wherein at least one of an evaluation circuit (30) and a heat regulating circuit (35) is located on said outer region (11) of said carrier plate (10).

13. The electrical hot gas sensor device of claim 11, wherein a plurality of heat regulating circuits is located on said outer region (11) of said carrier plate (10).

14. The electrical hot gas sensor device of claim 3, wherein at least one through contact (32) is provided passing through said carrier plate from said upper surface to said lower surface of said carrier plate (10) and is connected to said at least one temperature measuring resistance (26) for connecting the same with a circuit that lies at least in part on said upper surface of said carrier plate.

15. The electrical hot gas sensor device of claim 14, wherein at least one of an evaluation circuit (30) and a heat regulating circuit (35) is located on said outer region (11) of said carrier plate (10).

16. The electrical hot gas sensor device of claim 14, wherein a plurality of heat regulating circuits is located on said outer region (11) of said carrier plate (10).

17. The electrical hot gas sensor device of claim 1, in which a plurality of separately heatable sensor elements (1, 2) is provided on said carrier plate (10) each on a said middle region (12) where it is the only said sensor element on the respective middle region.

* * * * *